(12) United States Patent
Fung et al.

(10) Patent No.: US 6,200,329 B1
(45) Date of Patent: *Mar. 13, 2001

(54) SUTURE COLLET

(75) Inventors: Leo C. T. Fung, Southboro; Steven W. Ek, Bolton, both of MA (US)

(73) Assignees: Smith & Nephew, Inc., Memphis, TN (US); University of Massachusetts, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/143,591

(22) Filed: Aug. 31, 1998

(51) Int. Cl.$^7$ .................................................. A61B 17/04
(52) U.S. Cl. .............................................................. 606/232
(58) Field of Search ................................... 606/232, 144, 606/72, 73, 74, 139; 128/898, 899; 24/115 M, 136 R, 587, 399, 400

(56) References Cited

U.S. PATENT DOCUMENTS

| | | |
|---|---|---|
| 919,138 | 4/1909 | Drake et al. . |
| 1,037,864 | 9/1912 | Carlson et al. . |
| 1,635,066 | 7/1927 | Wells . |
| 1,815,725 | 7/1931 | Pilling et al. . |
| 2,610,631 | 9/1952 | Calicchio . |
| 2,665,597 | 1/1954 | Hill . |
| 2,880,728 | 4/1959 | Rights . |
| 3,013,559 | 12/1961 | Thomas . |
| 3,349,772 | 10/1967 | Rygg . |
| 3,470,875 | 10/1969 | Johnson . |
| 3,541,591 | 11/1970 | Hoegerman . |
| 3,638,653 | 2/1972 | Berry . |
| 3,664,345 | 5/1972 | Dabbs et al. . |
| 3,665,560 | 5/1972 | Bennett et al. ........................ 24/136 |

(List continued on next page.)

FOREIGN PATENT DOCUMENTS

| | | |
|---|---|---|
| 0 270 704 A1 | 6/1988 | (EP) . |
| 0 340 159 A1 | 3/1989 | (EP) . |
| 0 409 364 A2 | 1/1991 | (EP) . |
| 0 502 509 A1 | 9/1992 | (EP) . |
| 0 574 707 A1 | 12/1993 | (EP) . |
| 0 591 991 A2 | 4/1994 | (EP) . |
| 0707829 A1 | 4/1996 | (EP) . |
| 2 682 867 | 4/1993 | (FR) . |
| WO 95/02363 | 1/1995 | (WO) . |
| WO 95/32670 | 7/1995 | (WO) . |
| WO 95/29637 | 11/1995 | (WO) . |
| WO 97/30639 | 8/1997 | (WO) . |

OTHER PUBLICATIONS

Innovasive Devices, Inc., Product Information Sheet, ROC Fastener System.

Smith & Nephew Dyonics, Product Advertisement for PRO-LINE Reusable Endoscopic Hand Instruments.

Auto Suture Company, Product Advertisement, "Endoscopic suturing made easy", 1994.

Primary Examiner—Gary Jackson
Assistant Examiner—Vikki Hoa Trinh
(74) Attorney, Agent, or Firm—Fish & Richardson P.C.

(57) ABSTRACT

A suture securing device includes an inner member defining a suture receiving passage extending between a distal end surface of the inner member and a second surface of the inner member. An outer member defines an opening for receiving the inner member such that suture extending from the second surface is secured between the inner member and the outer member. The second surface is a proximal end surface of the inner member, and a slot extends between an outer surface of the inner member and the passage. Suture is threaded through the inner member in a proximal direction, and the outer member is advanced over the inner member to cause the suture to double back in a distal direction. A suture securing cartridge includes a sleeve having an axial bore with the suture securing device disposed in the bore.

38 Claims, 7 Drawing Sheets

U.S. PATENT DOCUMENTS

| | | |
|---|---|---|
| 3,752,516 | 8/1973 | Mumma . |
| 3,840,017 | 10/1974 | Violante . |
| 3,842,840 | 10/1974 | Schweizer . |
| 3,845,772 | 11/1974 | Smith . |
| 3,871,379 | 3/1975 | Clarke . |
| 3,901,244 | 8/1975 | Schweizer . |
| 3,910,281 | 10/1975 | Kletschka et al. . |
| 3,946,740 | 3/1976 | Bassett . |
| 3,976,079 | 8/1976 | Samuels et al. . |
| 4,161,951 | 7/1979 | Scanlan, Jr. . |
| 4,164,225 | 8/1979 | Johnson et al. . |
| 4,224,947 | 9/1980 | Fukuda . |
| 4,235,238 | 11/1980 | Ogiu et al. . |
| 4,287,807 | 9/1981 | Pacharis et al. . |
| 4,291,698 | 9/1981 | Fuchs et al. . |
| 4,312,337 | 1/1982 | Donohue . |
| 4,473,102 | 9/1984 | Ohman et al. ............. 160/345 |
| 4,493,323 | 1/1985 | Albright et al. . |
| 4,532,926 | 8/1985 | O'Holla . |
| 4,573,844 | 3/1986 | Smith . |
| 4,596,249 | 6/1986 | Freda et al. . |
| 4,602,635 | 7/1986 | Mulhollan et al. . |
| 4,621,640 | 11/1986 | Mulhollan et al. . |
| 4,641,652 | 2/1987 | Hutterer et al. . |
| 4,643,178 | 2/1987 | Nastari et al. . |
| 4,669,473 | 6/1987 | Richards et al. . |
| 4,719,671 | 1/1988 | Ito et al. ............................ 24/115 |
| 4,741,330 | 5/1988 | Hayhurst . |
| 4,744,353 | 5/1988 | McFarland . |
| 4,744,793 | 5/1988 | Parr et al. . |
| 4,750,492 | 6/1988 | Jacobs . |
| 4,779,616 | 10/1988 | Johnson . |
| 4,781,190 | 11/1988 | Lee . |
| 4,890,615 | 1/1990 | Caspari et al. . |
| 4,923,461 | 5/1990 | Caspari et al. . |
| 4,957,498 | 9/1990 | Caspari et al. . |
| 4,961,741 | 10/1990 | Hayhurst . |
| 5,078,731 | 1/1992 | Hayhurst ........................ 606/232 |
| 5,084,058 | 1/1992 | Li . |
| 5,087,263 | 2/1992 | Li . |
| 5,100,415 | 3/1992 | Hayhurst . |
| 5,100,418 | 3/1992 | Yoon et al. . |
| 5,100,421 | 3/1992 | Christoudias . |
| 5,133,723 | 7/1992 | Li et al. . |
| 5,149,329 | 9/1992 | Richardson . |
| 5,163,946 | 11/1992 | Li . |
| 5,176,691 | 1/1993 | Pierce . |
| 5,181,919 | 1/1993 | Bergman et al. . |
| 5,192,287 | 3/1993 | Fournier et al. . |
| 5,201,744 | 4/1993 | Jones . |
| 5,217,471 | 6/1993 | Burkhart . |
| 5,222,508 | 6/1993 | Contarini . |
| 5,224,946 | 7/1993 | Hayhurst . |
| 5,224,955 | 7/1993 | West . |
| 5,234,443 | 8/1993 | Phan et al. . |
| 5,234,444 | 8/1993 | Christoudias . |
| 5,250,054 | 10/1993 | Li . |
| 5,250,055 | 10/1993 | Moore et al. . |
| 5,257,637 | 11/1993 | El Gazayerli . |
| 5,258,015 | 11/1993 | Li et al. ........................... 606/232 |
| 5,259,846 | 11/1993 | Granger et al. . |
| 5,261,917 | 11/1993 | Hasson et al. . |
| 5,268,001 | 12/1993 | Nicholson et al. . |
| 5,269,783 | 12/1993 | Sander . |
| 5,269,791 | 12/1993 | Mayzels et al. . |
| 5,281,234 | 1/1994 | Wilk et al. . |
| 5,282,832 | 2/1994 | Toso et al. ....................... 606/232 |
| 5,324,308 | 6/1994 | Pierce . |
| 5,336,240 | 8/1994 | Metzler et al. . |
| 5,382,257 | 1/1995 | Lewis et al. . |
| 5,387,221 | 2/1995 | Bisgaard ......................... 606/148 |
| 5,389,103 | 2/1995 | Melzer et al. ................... 606/144 |
| 5,417,712 | 5/1995 | Whittaker et al. ............... 606/232 |
| 5,423,860 | 6/1995 | Lizardi et al. ................... 606/232 |
| 5,454,823 | 10/1995 | Richardson et al. ............. 606/148 |
| 5,458,601 | 10/1995 | Young, Jr. et al. . |
| 5,464,427 | * 11/1995 | Curtis et al. ..................... 606/232 |
| 5,480,403 | 1/1996 | Lee et al. . |
| 5,486,197 | 1/1996 | Le et al. . |
| 5,571,090 | 11/1996 | Sherts . |
| 5,573,548 | 11/1996 | Nazre et al. . |
| 5,578,044 | 11/1996 | Gordon et al. . |
| 5,584,835 | 12/1996 | Greenfield . |
| 5,630,824 | 5/1997 | Hart . |
| 5,643,321 | 7/1997 | McDevitt . |
| 5,645,552 | 7/1997 | Sherts . |
| 5,649,963 | 7/1997 | McDevitt . |
| 5,902,321 | * 5/1999 | Caspari et al. .................. 606/232 |
| 5,931,844 | * 8/1999 | Thompson et al. .............. 606/144 |

* cited by examiner

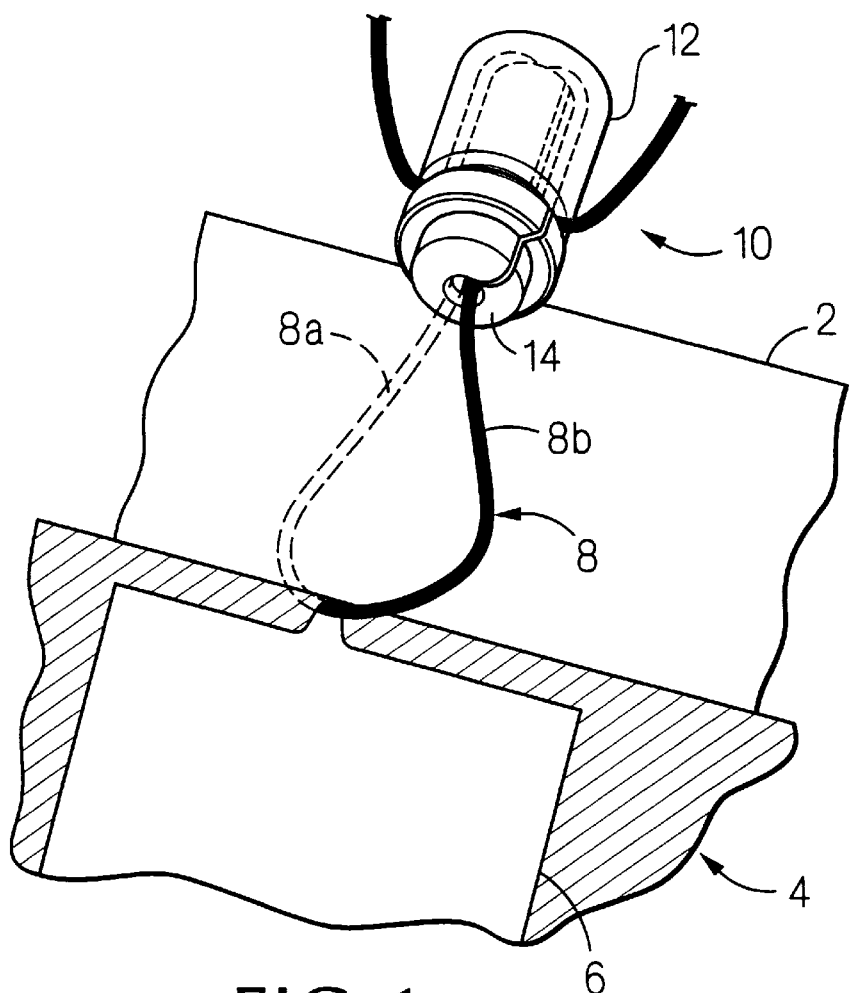
FIG. 1
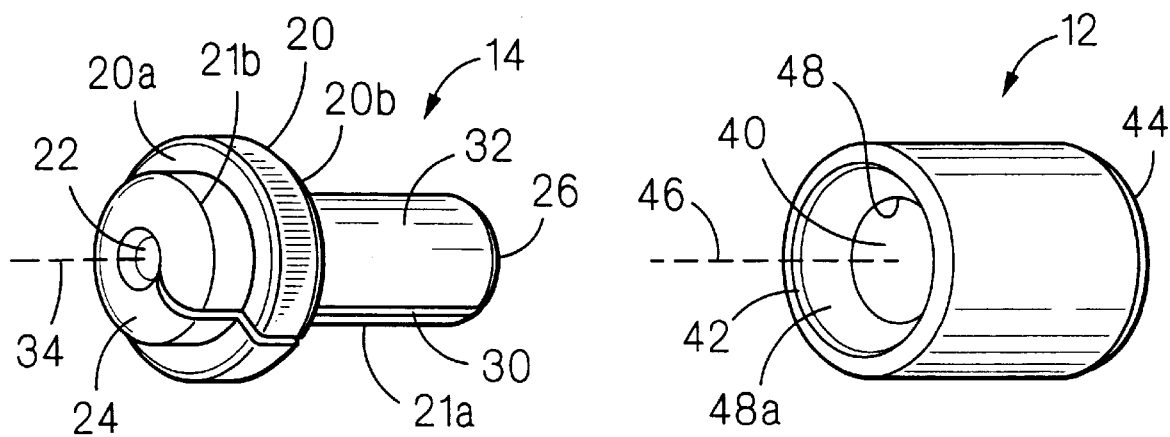
FIG. 2
FIG. 3

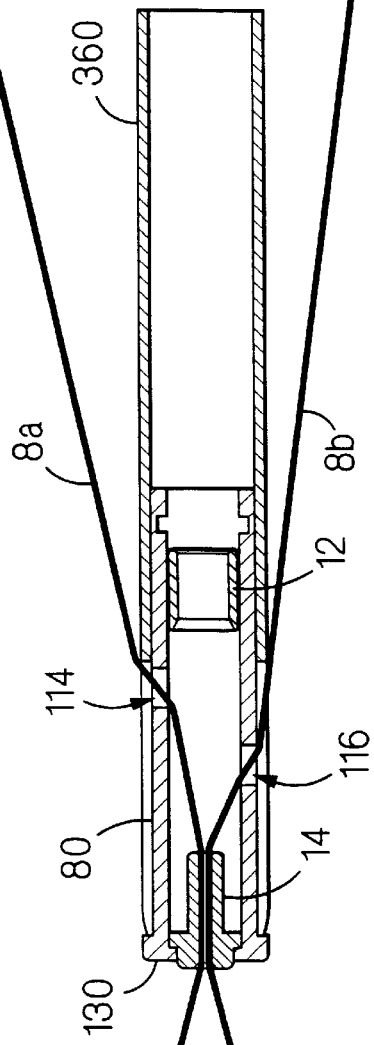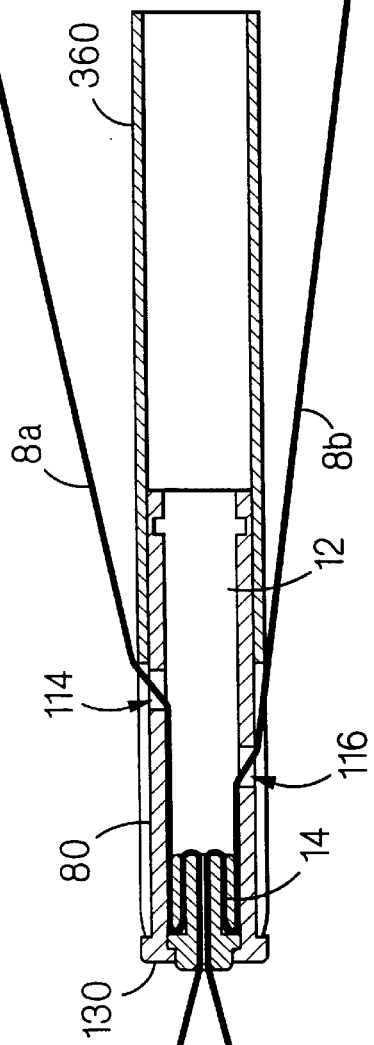

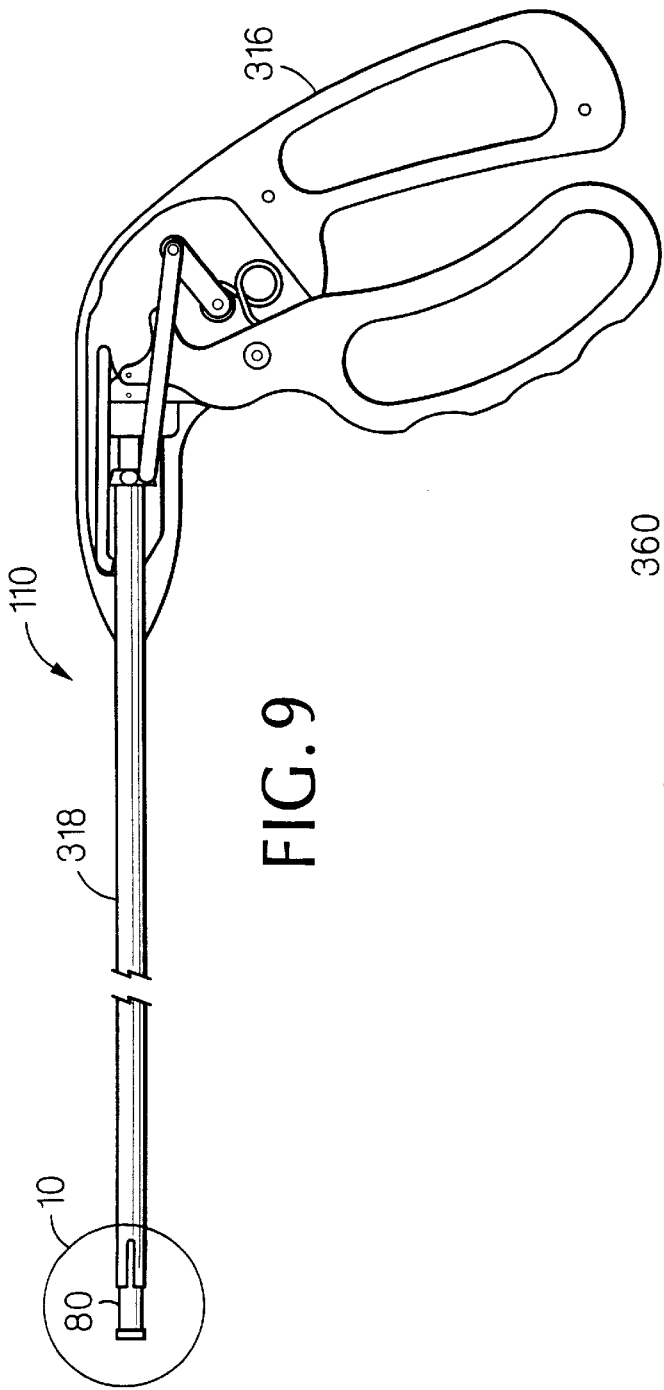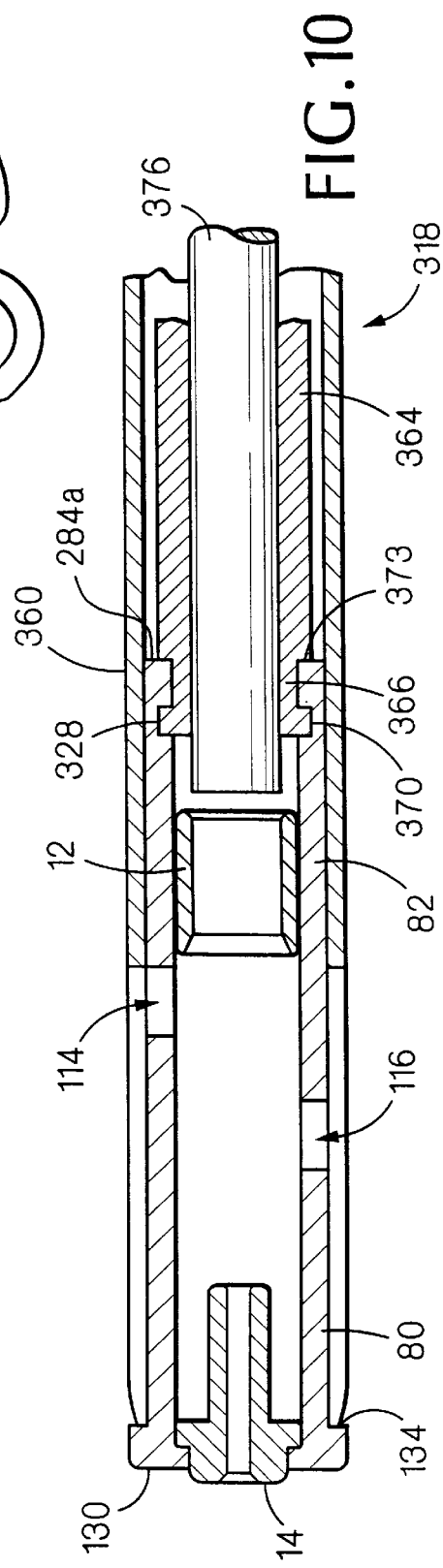

SUTURE COLLET

CROSS REFERENCE TO RELATED APPLICATIONS

This application is related to Ek, U.S. Ser. No. 08/915,758, filed Aug. 21, 1997, titled SUTURING TISSUE, Ek et al., U.S. Ser. No. 08/783,126, filed Jan. 14, 1997, titled SUTURE COLLET, Ek et al., U.S. Ser. No. 08/605,767, filed Feb. 22, 1996, titled SUTURE COLLET, and Thompson et al., U.S. Ser. No. 09/052,651, filed Mar. 31, 1998, titled SURGICAL DRIVE TOOL, all hereby incorporated herein by reference.

BACKGROUND OF THE INVENTION

This invention relates to suture fastening.

One traditional method of fastening suture is simply by tying a knot in the suture. Alternatively, a suture clamp may be used. In a typical suture clamp, the suture is positioned between an open pair of arms which are then pivoted closed to capture the suture between them.

SUMMARY OF THE INVENTION

A suture securing device includes an inner member defining a suture receiving passage extending between a distal end surface of the inner member and a second surface of the inner member. An outer member defines an opening for receiving the inner member such that suture extending from the second surface is secured between the inner member and the outer member.

Embodiments of this aspect of the invention may include one or more of the following features.

The second surface is a proximal end surface of the inner member. The inner member has a slot extending between an outer surface of the inner member and the suture receiving passage. A region of the inner member has an outer diameter greater than the diameter of the outer member bore. The inner member is cylindrical.

Preferably, the outer member bore extends axially from a proximal end to a distal end of the outer member. The outer member bore tapers distally from a smaller diameter to a larger diameter. The outer member is cylindrical.

According to another aspect of the invention, a suture securing cartridge includes a sleeve having an axial bore and a suture securing device disposed in the bore. The suture securing device includes an inner member defining a suture receiving passage, and an outer member disposed in the bore proximally of the inner member and configured for advancement over the inner member.

Embodiments of this aspect of the invention may include one or more of the following features.

The sleeve includes two suture threading slots extending proximally from a distal end of the sleeve. One of the slots terminates distally of the other slot. At least a portion of the slots extend along a longitudinal axis of the sleeve. The sleeve has a distal clamp for selectively preventing the inner member from exiting the sleeve bore in a distal direction. The clamp is resilient to permit the inner member to exit the bore in the distal direction.

According to another aspect of the invention, a suturing apparatus includes a suture securing cartridge and a drive tool. The drive tool includes an outer sheath which fits over the cartridge sleeve, an intermediate tube which engages the sleeve to secure the cartridge to the drive tool, and a movable element located within the intermediate tube for advancing the outer member over the inner member.

Embodiments of this aspect of the invention may include the sleeve having a circumferential groove in the bore, and the intermediate tube has a grasper which engages the groove to secure the cartridge to the drive tool.

According to another aspect of the invention, a method of securing a suture includes threading a suture through a passage in an inner member. The passage extends between a distal end surface of the inner member and a second surface of the inner member. An outer member is advanced over the inner member such that suture extending from the second surface is secured between the inner member and the outer member.

Embodiments of this aspect of the invention may include one or more of the following features.

Threading includes threading the suture in a proximal direction, and advancing the outer member over the inner member to cause the suture to double back in a distal direction. A first suture strand is passed through a first suture threading slot in a sleeve containing the inner member and the outer member, and through a slot in the inner member to the passage. An outer sheath is advanced over the sleeve to at least partially cover the first suture threading slot.

Preferably, a second suture strand is passed through a second suture threading slot in the sleeve, and through a slot in the inner member to the passage. The outer sheath is advanced over the sleeve to at least partially cover the second suture threading slot.

After advancing the outer member over the inner member, the inner and outer members are expelled from a sleeve containing the members.

According to another aspect of the invention, a method of using a suture securing device includes providing a preassembled suture securing cartridge including a sleeve having an axial bore and a suture securing device. The preassembled cartridge is inserted into a drive tool that includes an outer sheath which fits over the sleeve, an intermediate tube which engages the sleeve to secure the cartridge to the drive tool, and a movable element located within the intermediate tube. The movable element is advanced to advance the outer member over the inner member.

Embodiments of this aspect of the invention may include, after advancing the outer member over the inner member, expelling the inner member and the outer member from the sleeve.

We have found that the holding power of the suture securing device is substantially greater than that of a standard open surgical knot. The suture securing device also enables the surgeon to advance the suture securing device into the body to the site of the tissue being sutured and then position the suture within the suture securing device at the surgical site.

Other features and advantages of the invention will be apparent from the following detailed description, and from the claims.

BRIEF DESCRIPTION OF THE DRAWINGS

FIG. 1 shows a suture collet for securing suture;

FIG. 2 is a perspective view of an inner pin of the suture collet of FIG. 1;

FIG. 3 is a perspective view of an outer ring of the suture collet of FIG. 1;

FIG. 9 shows the drive tool of FIG. 5 in more detail; and

FIG. 10 is a cross-sectional view of the distal portion of the drive tool of FIG. 9.

DESCRIPTION OF THE PREFERRED EMBODIMENT

Figure 4:
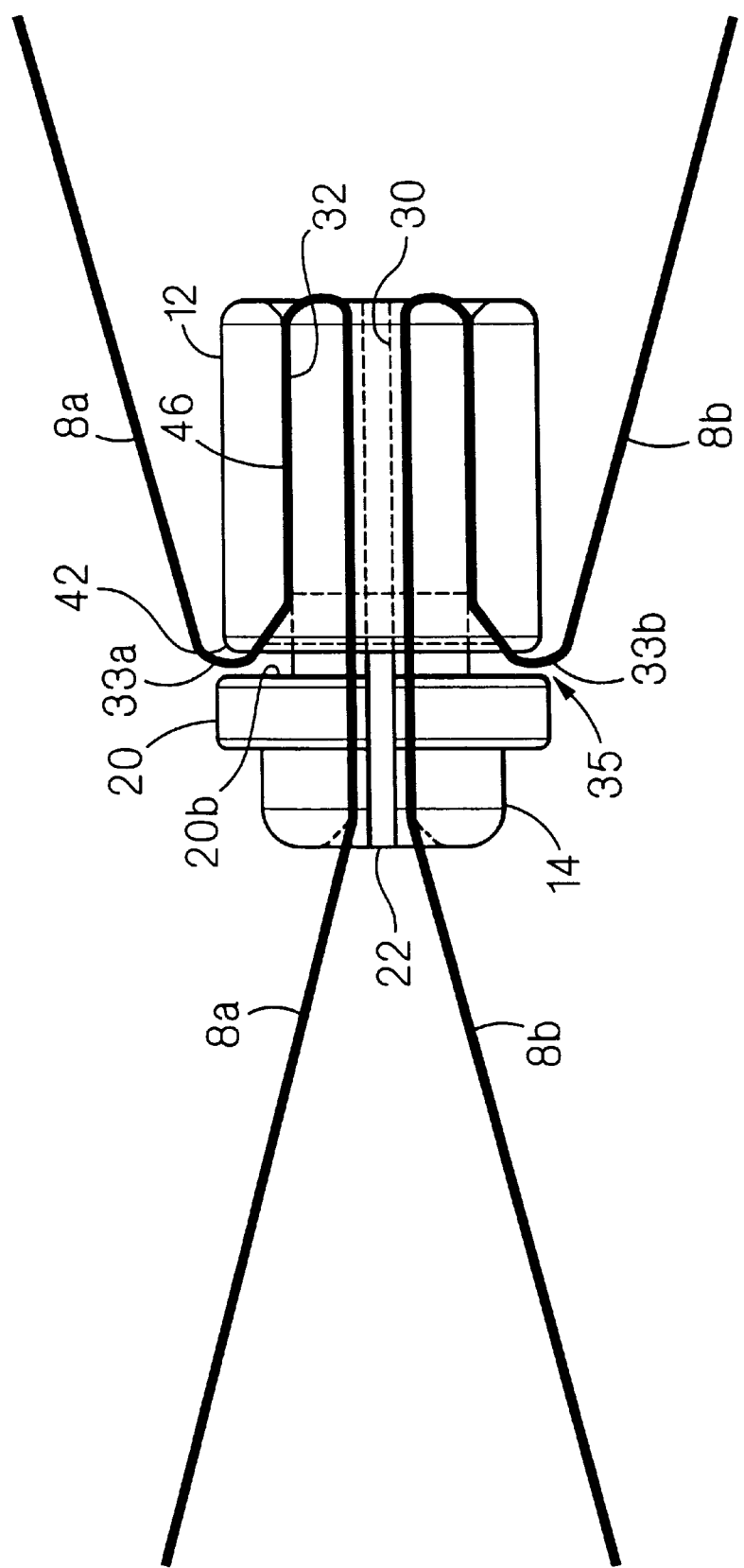
FIG. 4 is a side view of the suture collet of FIG. 1.

Referring to FIG. 1, a suture collet 10 is used in place of conventional securing techniques (e.g., knot tying) to secure a suture 8 in place. Suture collet 10 can be used in a wide variety of applications—in the operation shown schematically in FIG. 1, suture collet 10 clamps a loop of suture 8 in place between a ligament 2 and a bone 4 (suture 8 is attached to bone 4 by a suture anchor 6 or other suitable device). As discussed in more detail below, suture collet 10 includes an outer locking ring 12 and an inner locking pin 14 between which suture 8 is secured when outer ring 12 is advanced over pin 14.

Referring to FIG. 2, pin 14 is generally cylindrical in shape with a section 20 of enlarged outer diameter defining a distal shelf 20a and a proximal shelf 20b. On the proximal side of section 20 is a first portion 21a of pin 14, and on the distal side of section 20 is a second portion 21b of pin 14. Pin 14 has an axially-oriented, longitudinal passage 22 for receiving, e.g., two sections 8a, 8b (FIG. 1) of suture 8, though more than two suture sections can be used. Passage 22 extends completely through pin 14, from proximal surface 26 to distal surface 24, along a longitudinal central axis 34 of pin 14. A slot 30 extends from the outer surface 32 of pin 14 to passage 22. As described further below, suture sections 8a, 8b are positioned within passage 22 when pin 14 is located within the body by passing the suture sections through slot 30.

Referring to FIG. 3, ring 12 is generally cylindrical in shape and has an axially-oriented, longitudinal bore 40. Bore 40 extends completely through ring 12, from proximal end 44 to distal end 42, along a longitudinal central axis 46 of ring 12. Bore 40 is sized to receive the first portion 21a of pin 14, but is not large enough to receive section 20. The internal wall 48 of ring 12 defining bore 40 has an outwardly tapered, distal wall section 48a. The tapered wall section aids in aligning ring 12 over pin 14 when advancing the ring over the pin.

There is a close fit between the outer surface 32 of pin 14 and the internal wall 48 of ring 12 to clamp the suture therebetween. Additionally, the overall size of suture collet 10 with ring 12 positioned over pin 14 corresponds, e.g., approximately to the size of three successive throws of a suture knot. For example, ring 12 is about 0.15 inches long, has an outer diameter of about 0.125 inches and an inner diameter of about 0.07 inches; pin 14 is about 0.225 inches long, section 20 has an outer diameter of about 0.13 inches, section 21a has an outer diameter of about 0.07 inches, and section 21b has an outer diameter of about 0.094 inches. Passage 22 has a diameter of about 0.025 inches. Ring 12 and pin 14 can be made from a non-absorbable material such as polyacetal available from M. Holland Co., Northbrook, Ill., or a bio-absorbable material, such as Maxon, a polyglyconate, available from Davis & Geck.

Referring to FIG. 4, suture collet 10 clamps suture as follows. After suture sections 8a, 8b have been passed through slot 30 into passage 22 (a tool and procedure for doing so are described below) ring 12 is advanced over pin 14 so that suture sections 8a, 8b are looped back axially along the outer surface 32 of pin 14, and secured between internal wall 48 of ring 12 and outer surface 32 of pin 14. Advancement of ring 12 over pin 14 is stopped when the suture sections are compressed at looped regions 33a, 33b between distal end 42 of ring 12 and proximal surface 20b of enlarged pin section 20. The suture extends from suture collet 10 at the junction 35 of the ring and pin. The compression of the suture between the internal wall 48 of ring 12 and the outer surface 32 of pin 14 securely clamps the suture in place.

Figure 5:
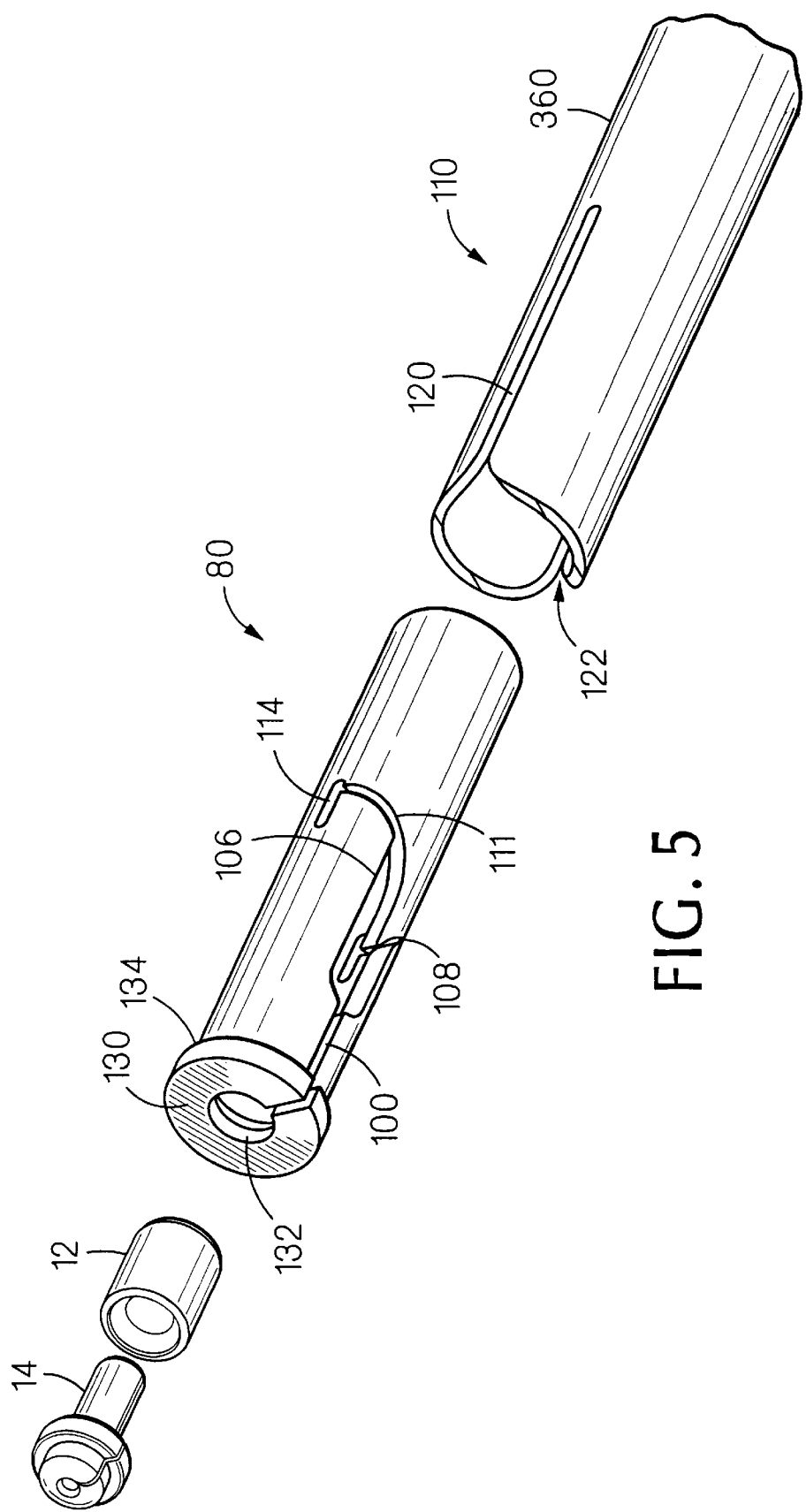
FIG. 5 is an exploded perspective view of the suture collet of FIG. 1 shown with a cartridge and drive tool.

FIG. 5 is an exploded view of instruments which can be used to emplace suture collet 10 in the body and advance ring 12 over pin 14 to clamp suture in place in the manner discussed above. Ring 12 and pin 14 are carried within a cartridge 80 (as shown in FIG. 6), and drive tool 110 including an outer sheath 360 is used to advance ring 12 over pin 14 and expel the suture collet from cartridge 80.

Figure 6:
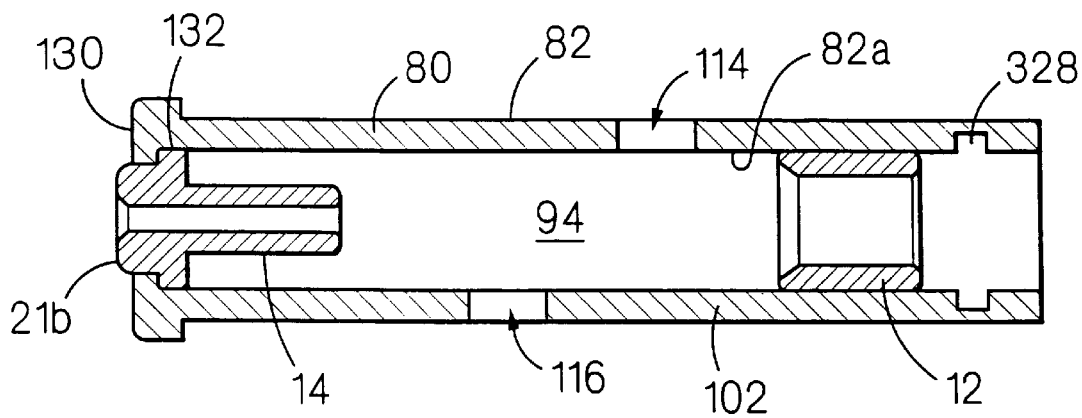
FIG. 6 is a cross-sectional view of the cartridge of FIG. 5 pre-loaded with the suture collet.
Figure 7:
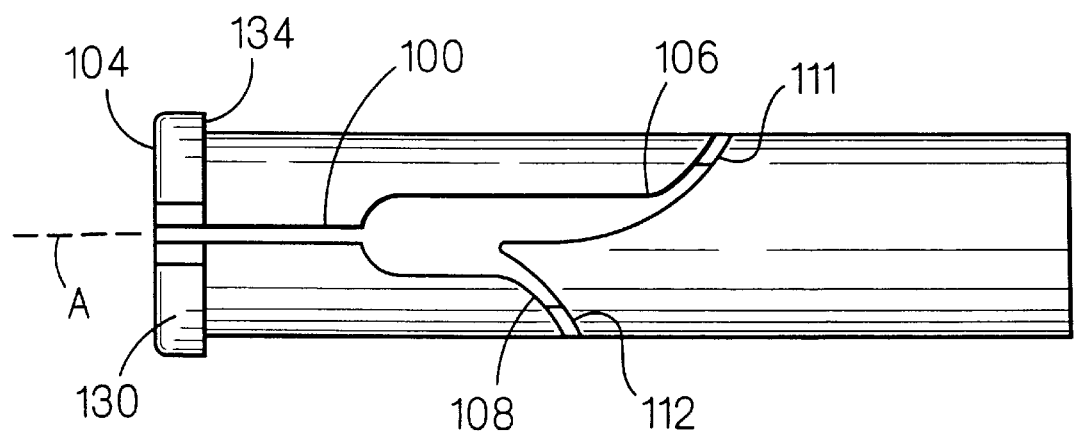
FIG. 7 is a side view of the cartridge of FIG. 5.

Referring also to FIGS. 6 and 7, cartridge 80 includes a hollow sleeve 82 the distal end of which is provided with a clamping lip 130 having a reduced diameter, internal shoulder 132 which receives distal section 21b of pin 14. The internal diameter of shoulder 132 is smaller than the diameter of enlarged section 20 such that suture collet pin 14 is held in place within cartridge 80.

The outer diameter of lip 130 is enlarged relative to that of the remainder of sleeve 82, such that an outer shoulder 134 is defined, for purposes to be discussed. As shown in FIG. 6, an axial passage 94 extends through sleeve 82. Ring 12 is supported within passage 94 by an interference fit with the inner wall surface 82a of passage 94 to maintain ring 12 axially spaced from pin 14 until it is to be advanced over pin 14. Sleeve 82 has a circumferential groove 328 in inner wall surface 82a proximally of ring 12 for purposes to be described.

Sleeve 82 has a suture threading slot 100 through sleeve wall 102 extending proximally from distal end 104 of sleeve 82 along a longitudinal axis A of sleeve 82. Slot 100 bifurcates into two threading slots 106, 108 each having a curved section 111, 112 terminating in an axial slot 114, 116, respectively. Axial slots 114, 116 are located circumferentially 90 degrees from slot 100 on opposite sides of sleeve 82. Slot 106 extends further proximally than slot 108. Pin 14 is loaded within sleeve 82 with pin slot 30 aligned with cartridge slot 100. Sheath 360 includes slots 120, 122 (FIG. 5) which are aligned with axial slots 114, 116. Slot 100 permits lip 130 of sleeve 82 to resiliently expand radially when suture collet 10 is to be expelled from the cartridge.

Referring to FIGS. 8A–8D, suture collet 10 is emplaced with drive tool 110 as follows. For example, as a preliminary step, suture 8 can be mounted to bone 4 with anchor 6 and passed through ligament 2 (FIG. 1). Multiple sutures can be mounted to the bone using multiple anchors prior to securing the sutures. Drive tool 110 with a cartridge 80 loaded with pin 14 and ring 12 is then advanced intracorporally, for example, through a conventional trocar used in arthroscopic or laproscopic surgery, to the fixation site. A single portal can be used to secure multiple sutures.

To secure a suture, sheath 360 is withdrawn proximally in the direction of arrow 124 while cartridge 80 is held stationary, as described below, to expose slots 106, 108. The user then passes section 8a of suture 8 through slot 106 and rotates drive tool 110, which rotates cartridge 80. Rotation of cartridge 80 results in curved section 111 of slot 106 guiding suture section 8a into axial slot 114. Since axial slot 114 is located circumferentially 90 degrees from slot 100, when suture section 8a is moved into slot 114, the suture section also passes through pin slot 30 into passage 22.

Figure 8A:
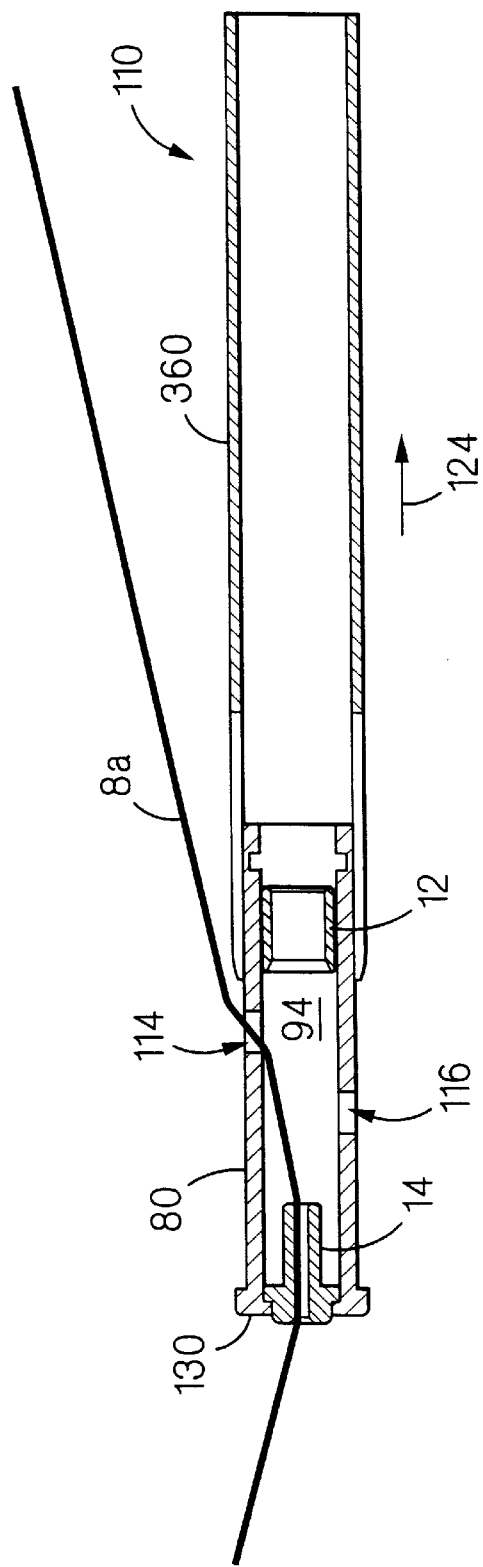
FIGS. 8–8D show the drive tool in use with the suture collet and cartridge.
Figure 8B:
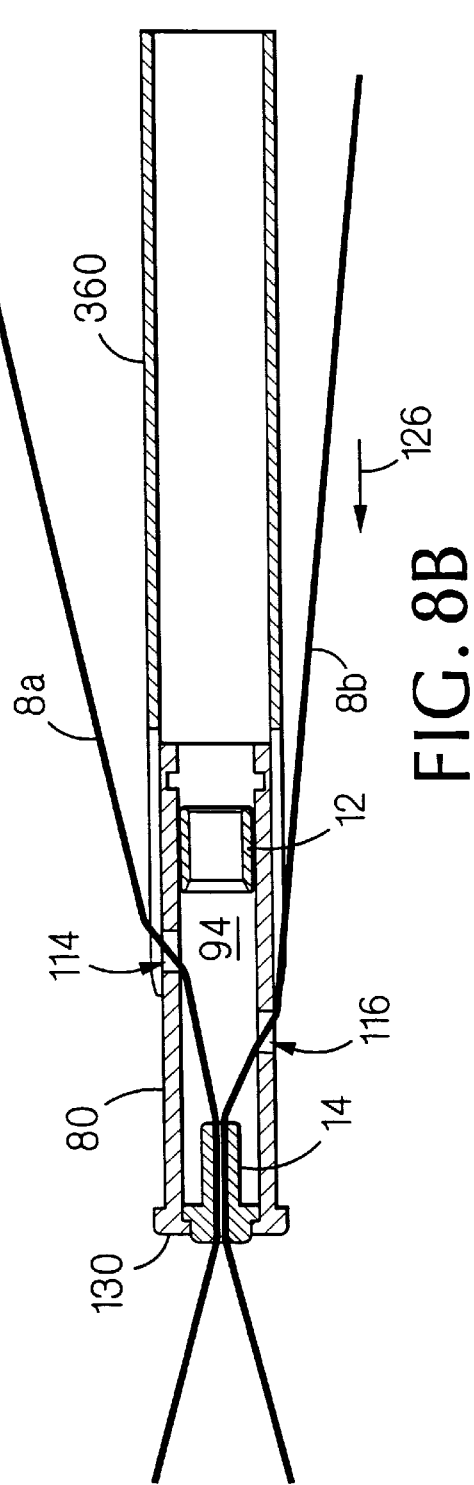

Referring to FIG. 8B, the user then advances sheath 360 distally in the direction of arrow 126 with sheath slot 120 aligned with axial slot 114 to trap strand 8a within axial slot 114. The sheath is not advanced as far as slot 108 such that slot 108 remains exposed. The user then passes strand 8b of suture 8 through slot 108 and rotates sheath 360 to lodge suture strand 8a in axial slot 116, and thus through pin slot 30 into passage 22. Sheath 360 is then advanced fully distally in the direction of arrow 126 to trap strand 8b within axial slot 116, as shown in FIG. 8C. At this point, suture section 8a, 8b are disposed within pin passage 22 and extend out of proximal surface 26. Referring to FIG. 8D, the user then advances ring 12 over pin 14, as described below.

Note that the placement of suture 8 within pin 14 acts as the first throw of the suture knot to reduce the tissue and allows sliding travel of the suture much like the first throw of a conventional knot. The frictionless contact between pin 14 and the suture permits the surgeon to feel how much tension is being put into the tissue even more precisely than the first throw of a conventional knot which has some friction. This is particularly advantageous when suturing vessels with thin walls or suturing delicate tissue. In addition, the tension on the suture, instead of acting to pull the suture loose, increases the holding force on the suture applied by suture collet 10.

Referring to FIG. 9, drive tool 110 includes a handle assembly 316 and a tube assembly 318. To position suture collet 10 at a surgical site, the cartridge assembly is secured to drive tool 110; the drive tool is advanced to the surgical site and the user manipulates the drive tool to deploy the suture collet from the cartridge assembly, as described in Thompson et al., U.S. Ser. No. 09/052,651, supra.

Referring also to FIG. 10, tube assembly 318 of drive tool 110 includes outer sheath 360 which fits over sleeve 82 of the cartridge assembly. A grasper 364 located within sheath 360 has a circumferential groove 366 with a distal ridge 370 configured to fit within groove 328 of sleeve 82, and a shoulder 373 which engages proximal end 294a of sleeve 82 to secure cartridge 80 within drive tool 110.

A plunger 376 is slidable within grasper 364 and engages ring 12 pushing it over pin 14. Plunger 376 and outer sheath 360 are moved by manipulating handle assembly 316 of drive tool 110, as described in Thompson et al., U.S. Ser. No. 09/052,651, supra. Pushing ring 12 over pin 14 causes suture strands 8a, 8b to double back distally securing the strands between internal wall 48 of ring 12 and outer surface 32 of pin 14.

The suture collet with clamped suture is removed from cartridge 80 simply by retracting sheath 360 axially away from shoulder 134 and advancing plunger 376 distally. With sheath 360 retracted, lip 130 of cartridge 80 flexes outwardly as suture collet 10 is moved distally thereby permitting plunger 376 to push suture collet 10 distally from cartridge 80.

Other embodiments are within the scope of the following claims. For example, rather than the suture passage in the pin emerging from the proximal end of the pin, the suture passage can emerge from the side of the pin. t least one of the slots 120, 122 in sheath 360 can be eliminated or its length decreased, such that the suture strand is crimped between the sleeve and the sheath. With one strand of the suture crimped, only the other strand need be pulled to tighten the suture.

Slots 106, 108 of sleeve 82 can extend proximally the same distance. Slot 100 of sleeve 82 need not bifurcate into two slots such the suture strands are positioned within a single slot. Slot 100 can be straight rather than include one or more curved sections.

Suture collet 10 can be used wherever a suture knot would be tied, for example, in ligating branches of vessels, in soft-tissue repair, in reducing tissues, and in securing other types of tissue to bone.

Other materials can be used according to the suturing application. Ring 12 and pin 14 can be shaped other than cylindrical. More than two suture strands can be secured with the collet.

What is claimed is:

1. A suture securing device, comprising:
   an inner member defining a suture receiving passage extending proximally from a distal end surface of the inner member configured to face tissue being sutured to a second surface of the inner member, the inner member defining a slot extending proximally from the distal end surface and radially from the suture receiving passage to an outer surface of the inner member to permit suture to be passed therethrough into the suture receiving passage, and
   an outer member defining an opening for receiving the inner member, the opening being sized relative to the inner member to define a gap between the inner member and the outer member for receiving the suture such that a portion of the suture extending from the second surface is secured between the inner member and the outer member.

2. The suture securing device of claim 1 wherein the second surface comprises a proximal end surface of the inner member.

3. The suture securing device of claim 1 wherein the outer member opening comprises a bore and the inner member includes a region having an outer diameter greater than a diameter of the outer member bore.

4. The suture securing device of claim 1 wherein the inner member is cylindrical.

5. The suture securing device of claim 1 wherein the outer member opening comprises a bore extending axially from a proximal end to a distal end of the outer member.

6. The suture securing device of claim 1 wherein the outer member opening comprises a bore tapering distally from a first diameter to a second diameter, the second diameter being larger than the first diameter.

7. The suture securing device of claim 1 wherein the outer member is cylindrical.

8. The suture securing device of claim 1 wherein the inner member includes a collar having a first diameter and a distal end having a second diameter less than the first diameter.

9. A suture securing cartridge, comprising:
   a sleeve having an axial bore, and
   a suture securing device including an inner member disposed in the bore at a distal end of the sleeve, the inner member defining a suture receiving passage, and an outer member disposed in the bore proximally of the inner member with a distal-most end surface of the outer member spaced from a proximal-most end surface of the inner member, the outer member configured for advancement over the inner member.

10. The suture securing cartridge of claim 9 wherein the sleeve includes a first suture threading slot extending proximally from a distal end of the sleeve.

11. The suture securing cartridge of claim 10 wherein at least a portion of the first suture threading slot extends along a longitudinal axis of the sleeve.

12. The suture securing cartridge of claim 10 wherein the sleeve includes a second suture threading slot extending proximally from the distal end of the sleeve.

13. The suture securing cartridge of claim 12 wherein at least a portion of the first and second suture threading slots extend along a longitudinal axis of the sleeve.

14. The suture securing cartridge of claim 12 wherein the second suture threading slot terminates distally of the first suture threading slot.

15. The suture securing cartridge of claim 9 wherein the sleeve has a distal clamp for limiting distal movement of the inner member.

16. The suture securing cartridge of claim 15 wherein the distal clamp is resilient to permit the inner member to exit the bore in the distal direction.

17. The suture securing cartridge of claim 9, wherein the suture receiving passage extends from a distal end surface of the inner member to a proximal end surface of the inner member, the outer member defining an opening for receiving the inner member; the opening being sized to allow a portion of the suture that extends from the distal end surface of the inner member to the proximal end surface of the inner member to be looped back along substantially a full length of the outer member between the inner member and the outer member, the opening and the inner member being sized to frictionally secure the portion of suture between the inner member and the outer member when the inner member is received within the opening.

18. The suturing apparatus of claim 17, wherein
the suture receiving passage extends from a distal end surface of the inner member to a proximal end surface of the inner member, the outer member defining an opening for receiving the inner member; the opening being sized to allow a portion of the suture that extends from the distal end surface of the inner member to the proximal end surface of the inner member to be doubled back along substantially a full length of the outer member between the inner member and the outer member, the opening and the inner member being sized to frictionally secure the portion of suture between the inner member and the outer member when the inner member is received within the opening.

19. A suturing apparatus comprising:
a suture securing cartridge that includes
a sleeve having an axial bore, and
a suture securing device including an inner member disposed in the bore at a distal end of the sleeve, the inner member defining a suture receiving passage, and an outer member disposed in the bore proximally of the inner member with a distal-most end surface of the outer member spaced from a proximal-most end surface of the inner member, the outer member configured for advancement over the inner member,
a drive tool that includes
an outer sheath which fits over the sleeve, an intermediate tube which engages the sleeve to secure the cartridge to the drive tool, and a movable element located within the intermediate tube for advancing the outer member over the inner member.

20. The suturing apparatus of claim 19 wherein the sleeve has a circumferential groove in the bore, and the intermediate tube has a grasper which engages the groove to secure the cartridge to the drive tool.

21. A method of securing a Suture, comprising:
passing a first suture strand through a first suture threading slot in a sleeve,
passing the first suture strand through a passage in an inner member positioned within the sleeve, the passage extending between a distal end surface of the inner member and a second surface of the inner member, and
advancing an outer member over the inner member such that suture extending from the second surface is secured between the inner member and the outer member, the outer member being positioned within the sleeve proximally of the inner member with a distal-most end surface of the outer member spaced from a proximal-most end surface of the inner member.

22. The method of claim 21 wherein threading includes threading the suture in a proximal direction, and advancing the outer member over the inner member causes the suture to double back in a distal direction.

23. The method of claim 21 wherein threading further includes passing the first suture strand through a slot in the inner member to the passage.

24. The method of claim 21 further comprising advancing an outer sheath over the sleeve to at least partially cover the first suture threading slot.

25. The method of claim 21 further comprising passing a second suture strand through a second suture threading slot in the sleeve.

26. The method of claim 25 further comprising passing the second suture strand through a slot in the inner member to the passage.

27. The method of claim 25 further comprising advancing the outer sheath over the sleeve to at least partially cover the second suture threading slot.

28. The method of claim 21 further comprising, after advancing the outer member over the inner member, expelling the inner member and the outer member from a sleeve containing the inner member and the outer member.

29. A method of using a suture securing device, comprising:
providing a preassembled suture securing cartridge including a sleeve having an axial bore and a suture securing device, the suture securing device including an inner member disposed in the bore at a distal end of the sleeve, the inner member defining a suture receiving passage, and an outer member disposed in the bore proximally of the inner member with a distal-most end surface of the outer member spaced from a proximal-most end surface of the inner member, the outer member configured for advancement over the inner member,
inserting the preassembled cartridge into a drive tool that includes an outer sheath which fits over the sleeve, an intermediate tube which engages the sleeve to secure the cartridge to the drive tool, and a movable element located within the intermediate tube for advancing the outer member over the inner member, and
advancing the movable element to advance the outer member over the inner member.

30. The method of claim 29 further comprising, after advancing the outer member over the inner member, expelling the inner member and the outer member from the sleeve.

31. A suture securing device, comprising:
an inner member defining a suture receiving passage extending from a distal end surface of the inner member to a second surface of the inner member, and
an outer member defining an opening for receiving the inner member such that suture extending from the second surface is secured between the inner member and the outer member, the outer member opening tapering distally from a first diameter to a second diameter, the second diameter being larger than the first diameter, the outer member being sized for dwelling within a patient's body.

32. A suture securing device, comprising:

an inner member defining a suture receiving passage extending from a distal end surface of the inner member to a proximal end surface of the inner member, and an outer member defining an opening for receiving the inner member, the opening being sized to allow a portion of the suture that extends from the distal end surface of the inner member to the proximal end surface of the inner member to be looped back along substantially a full length of the outer member between the inner member and the outer member, the inner member and the outer member sized to be secured together by a friction fit with the portion of suture therebetween when the inner member is received within the opening.

33. The suture securing device of claim 32 wherein the inner member further defines a slot extending from the distal end surface to the proximal end surface and radially from the suture receiving passage to an outer surface of the inner member.

34. The suture securing device of claim 32 wherein the outer member opening comprises a bore and the inner member includes a region having an outer diameter greater than a diameter of the outer member bore.

35. The suture securing device of claim 32 wherein the outer member opening comprises a bore extending axially from a proximal end to a distal end of the outer member.

36. The suture securing device of claim 32 wherein the outer member opening comprises a bore tapering distally from a first diameter to a second diameter, the second diameter being larger than the first diameter.

37. A method of securing a suture, comprising:

passing a first suture strand through a first suture threading slot in a sleeve containing an inner member and an outer member, passing the first suture strand through a slot in the inner member to a passage in the inner member extending from a distal end surface of the inner member to a proximal end surface of the inner member, advancing an outer sheath over the sleeve to at least partially cover the first suture threading slot in the sleeve, passing a second suture strand through a second suture threading slot in the sleeve, passing the second suture strand through the slot in the inner member to the passage, and further advancing the outer sheath over the sleeve to at least partially cover the second suture threading slot in the sleeve.

38. The method of claim 37, further comprising advancing the outer member over the inner member such that the suture extending from the proximal end surface of the inner member loops back along substantially a full length of the outer member and is frictionally secured between the inner member and the outer member.

* * * * *

UNITED STATES PATENT AND TRADEMARK OFFICE
CERTIFICATE OF CORRECTION

PATENT NO. : 6,200,329 B1
DATED : March 13, 2001
INVENTOR(S) : Steven Ek and Leo C.T. Fung It is certified that error appears in the above-identified patent and that said Letters Patent is hereby corrected as shown below:

Column 5,
Line 62, replace "pin.t" with -- pin. At --.

Column 7, claim 21,
Line 63, replace "Suture" with -- suture --.

Signed and Sealed this

Eleventh Day of December, 2001

Attest:

NICHOLAS P. GODICI
Attesting Officer    Acting Director of the United States Patent and Trademark Office